US008765718B2

(12) United States Patent
Matsuzawa et al.

(10) Patent No.: US 8,765,718 B2
(45) Date of Patent: Jul. 1, 2014

(54) COSMETIC PREPARATION COMPRISING SILICONE

(75) Inventors: Makoto Matsuzawa, Yokohama (JP); Masaaki Fujisawa, Yokohama (JP); Keiichi Oyama, Yokohama (JP)

(73) Assignee: The Nisshin OilliO Group, Ltd., Tokyo (JP)

( * ) Notice: Subject to any disclaimer, the term of this patent is extended or adjusted under 35 U.S.C. 154(b) by 358 days.

(21) Appl. No.: 12/666,881

(22) PCT Filed: Jun. 24, 2008

(86) PCT No.: PCT/JP2008/061478
§ 371 (c)(1),
(2), (4) Date: Dec. 28, 2009

(87) PCT Pub. No.: WO2009/004952
PCT Pub. Date: Jan. 8, 2009

(65) Prior Publication Data
US 2010/0189676 A1      Jul. 29, 2010

(30) Foreign Application Priority Data

Jun. 29, 2007   (JP) .................................. 2007-173001

(51) Int. Cl.
| | | |
|---|---|---|
| A61K 8/37 | (2006.01) | |
| A61K 8/89 | (2006.01) | |
| A61K 8/891 | (2006.01) | |
| A61K 8/06 | (2006.01) | |
| A61Q 1/14 | (2006.01) | |
| A61Q 5/06 | (2006.01) | |

(52) U.S. Cl.
USPC .......................................... 514/63; 424/70.1

(58) Field of Classification Search
CPC ........... A61K 8/06; A61K 8/89; A61K 8/375; A61Q 1/14; A61Q 5/06
USPC .......................................... 424/70.1; 514/63
See application file for complete search history.

(56) References Cited

U.S. PATENT DOCUMENTS

| | | | | |
|---|---|---|---|---|
| 6,019,991 | A * | 2/2000 | Tanaka et al. .................. | 424/401 |
| 2005/0129649 | A1 * | 6/2005 | Kurosawa et al. ......... | 424/70.12 |
| 2006/0062752 | A1 | 3/2006 | Gotou et al. | |
| 2006/0067902 | A1 | 3/2006 | Gotou et al. | |
| 2007/0190002 | A1 | 8/2007 | Gotou et al. | |
| 2007/0264292 | A1 * | 11/2007 | Kurosawa et al. ............ | 424/401 |

FOREIGN PATENT DOCUMENTS

| | | | |
|---|---|---|---|
| JP | 288008 | * | 10/1992 |
| JP | 2002-255739 | * | 9/2002 |
| JP | 2003-137728 | * | 5/2003 |
| JP | 2004-196173 | * | 7/2004 |
| JP | 2004-339093 | A | 12/2004 |
| JP | 2004-339094 | A | 12/2004 |
| JP | 2004-339095 | A | 12/2004 |
| JP | 2004-339096 | A | 12/2004 |
| JP | 2004-339097 | A | 12/2004 |
| JP | 2004-339099 | A | 12/2004 |
| JP | 2004-339100 | A | 12/2004 |
| JP | 2004-339121 | A | 12/2004 |
| JP | 2004-339125 | A | 12/2004 |
| JP | 2004-339127 | A | 12/2004 |
| JP | 2004-339130 | A | 12/2004 |
| JP | 2004-339295 | A | 12/2004 |
| WO | WO 03/082454 | A1 | 10/2003 |
| WO | WO 2004/100902 | A1 | 11/2004 |
| WO | WO 2004/100917 | A1 | 11/2004 |

OTHER PUBLICATIONS

Machine Translation of JP 2004-339094; Published Dec. 2, 2004.*
International Search Report for PCT/JP2008/061478 completed Sep. 29, 2008.
Written Opinion for PCT/JP2008/061478 completed Sep. 29, 2008.

* cited by examiner

*Primary Examiner* — Rachael E Bredefeld
(74) *Attorney, Agent, or Firm* — Buchanan Ingersoll & Rooney PC

(57) ABSTRACT

The present invention discloses a cosmetic preparation which comprises 20 mass % or more of an oil ingredient comprising the following components (A) and (B), and said oil ingredient comprising 50 mass % or more of the component (B):
(A): one or more members selected from the group consisting of an ester compound(s) represented by the following formula (I) and/or formula (II) of erythritol and/or erythritol condensate with a fatty acid(s); polycondensates of erythritol and/or erythritol condensate, the above-mentioned ester compound(s) and a polycarboxylic acid(s); polycondensates of a fatty acid(s) with a polycondensate(s) of erythritol and/or erythritol condensate with a polycarboxylic acid(s); and polycondensates of erythritol and/or erythritol condensate, a fatty acid(s) and a polycarboxylic acid(s); and
(B): silicone.
This cosmetic preparation is excellent in compatibility with an oil agent and affinity for a water-base component. Particularly, the cosmetic preparation is excellent in compatibility with an oil agent and affinity for a water-base component even if the content of silicone is high.

7 Claims, No Drawings

COSMETIC PREPARATION COMPRISING SILICONE

TECHNICAL FIELD OF THE INVENTION

The present invention relates to a cosmetic preparation that various problems induced by comprising silicone therein are solved; and particularly it relates to a cosmetic preparation which can be preferably used as a water-in-oil cream, a two-layer separative makeup remover, and the like.

BACKGROUND OF THE INVENTION

Silicone (silicone oil and silicone surfactants) has the advantage that it is highly safe and excellent in heat resistance and water repellency. Further, silicone has a good feeling (light touch) in use and smoothly spreads on skin or hair, and it is excellent in water resistance, emulsion stability, detergency and feeling after washing. Therefore, particularly in the field of cosmetic preparations, silicone is widely used as makeup cosmetic preparations such as foundations and lipsticks; skin-care cosmetic preparations such as emulsions and creams; hair-care cosmetic preparations such as shampoos and rinses; and sunscreen agents.

On the other hand, since silicone is poorly compatible with an oil agent, when combining silicone with an oil agent, the combination amount of silicone or the oil agent is limited. Further, silicone has a low affinity for a water-base component. Therefore, when combining silicone with a formulation wherein an oil phase and a water phase normally separate and they are shaken in use such as a two-layer separative makeup remover, it is difficult to sustain the emulsified state by combination of silicone only, and the oil phase and the water phase quickly separate. Accordingly, it is required to further combine a component which has a high affinity for a water-base component or a surfactant (an emulsifying agent).

Thus, until now, the used amount of silicone has been limited, or a component which is compatible with silicone and excellent in an affinity for a water-base component has been used, such as an oil agent like diisostearyl malate. However, since diisostearyl malate has a high viscosity and the touch thereof in use becomes thicker, the good feeling (light touch) of silicone, which is the advantage when using silicone, is impaired by combining diisostearyl malate.

Meanwhile, it is already known to combine an ester compound(s) of erythritol and/or erythritol condensate with a fatty acid(s), or polycondensate(s) thereof as an oil agent in a cosmetic preparation (see Patent Literatures 1-12, for example). Though these patents disclose that the above ester compound(s) or polycondensate(s) thereof is used as an oil agent and combined with silicone, many of them intend to make an appeal for the excellent particulate (pigmentary) dispersibility of the above ester compound(s) or polycondensate(s) thereof. Thus, they neither disclose nor indicate that the problems such as the poor compatibility of silicone with an oil agent and the low affinity thereof for a water-base component can be solved by combining an oil agent(s) which is the above ester compound(s) or polycondensate(s) thereof with silicone.

Patent Literature 1: WO2003/082454
Patent Literature 2: WO2004/100902
Patent Literature 3: WO2004/100917
Patent Literature 4: JP 2004-339093 A
Patent Literature 5: JP 2004-339094 A
Patent Literature 6: JP 2004-339095 A
Patent Literature 7: JP 2004-339100 A
Patent Literature 8: JP 2004-339096 A
Patent Literature 9: JP 2004-339097 A
Patent Literature 10: JP 2004-339099 A
Patent Literature 11: JP 2004-339295 A
Patent Literature 12: JP 2004-339121 A

DISCLOSURE OF THE INVENTION

The object of the present invention is to provide a cosmetic preparation which is excellent in compatibility with an oil agent and affinity for a water-base component when using silicone as an essential component; and particularly, the cosmetic preparation which is excellent in compatibility with an oil agent and affinity for a water-base component even if the content of silicone is high.

The further object of the present invention is to provide a two-layer separative makeup remover and a two-layer separative hair dressing each of which has excellent characteristics without combining a surfactant.

The present invention has been completed based on the finding that the above problems can be solved by selecting a specific ester compound(s) of erythritol and/or erythritol condensate with a fatty acid(s), or polycondensate(s) thereof as an oil agent from various oil agents for a cosmetic preparation; and combining a specific amount thereof with silicone.

Namely, the present invention provides a cosmetic preparation which comprises 20 mass % or more of an oil ingredient comprising the following components (A) and (B), and said oil ingredient comprising 50 mass % or more of the component (B):

(A): one or more members selected from the group consisting of an ester compound(s) represented by the following formula (I) and/or formula (II) of erythritol and/or erythritol condensate with a fatty acid(s); polycondensates of erythritol and/or erythritol condensate, the above-mentioned ester compound(s) and a polycarboxylic acid(s); polycondensates of a fatty acid(s) with a polycondensate(s) of erythritol and/or erythritol condensate with a polycarboxylic acid(s); and polycondensates of erythritol and/or erythritol condensate, a fatty acid(s) and a polycarboxylic acid(s),

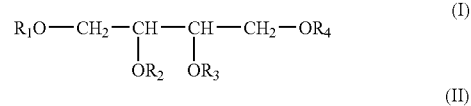

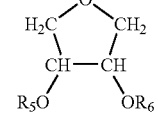

wherein $R_1$ to $R_4$ are each independently hydrogen atom, a fatty acid residue or a polycarboxylic acid residue, and $R_5$ and $R_6$ are each independently hydrogen atom, a fatty acid residue or a polycarboxylic acid residue; and (B): silicone.

The present invention also provides a two-layer separative makeup remover and a two-layer separative hair dressing each of which comprises the oil ingredient comprising the above components (A) and (B).

According to the present invention, it is possible to combine a high concentration of silicone in a cosmetic preparation, and it is also possible to obtain a cosmetic preparation having a good feeling in use because such good feeling of silicone is not impaired even if silicone is combined therein in high concentrations. In addition, even if a high concentration of silicone is combined in a two-layer separative makeup remover or a two-layer separative hair dressing, it is possible to sustain the emulsified state thereof in use without a surfactant. Thus, the present invention has a remarkable practical advantage that a formulation without a surfactant can be accomplished.

BEST MODE FOR CARRYING OUT THE INVENTION

The fatty acid for constituting the component (A) used in the present invention may preferably be a straight-chain or branched fatty acid having 5 to 28 carbon atoms. More preferably used are branched fatty acids. Examples of those branched fatty acids are pivalic acid, isoheptanoic acid, 4-ethylpentanoic acid, isooctylic acid, 2-ethylhexanoic acid, 4,5-dimethylhexanoic acid, 4-propylpentanoic acid, isononanoic acid, 2-ethylheptanoic acid, 3,5,5-trimethylhexanoic acid, isodecanoic acid, isododecanoic acid, 2-methyldecanoic acid, 3-methyldecanoic acid, 4-methyldecanoic acid, 5-methyldecanoic acid, 6-methyldecanoic acid, 7-methyldecanoic acid, 9-methyldecanoic acid, 6-ethylnonanoic acid, 5-propyloctanoic acid, isolauric acid, 3-methylhendecanoic acid, 6-propylnonanoic acid, isotridecanoic acid, 2-methyldodecanoic acid, 3-methyldodecanoic acid, 4-methyldodecanoic acid, 5-methyldodecanoic acid, 11-methyldodecanoic acid, 7-propyldecanoic acid, isomyristic acid, 2-methyltridecanoic acid, 12-methyltridecanoic acid, isopalmitic acid, 2-hexyldecanoic acid, 14-methylpentadecanoic acid, 2-ethyltetradecanoic acid, isostearic acid, methyl-branched isostearic acid, 2-heptylundecanoic acid, 2-isoheptylisoundecanoic acid, 2-ethylhexadecanoic acid, 14-ethylhexadecanoic acid, 14-methylheptadecanoic acid, 15-methylheptadecanoic acid, 16-methylheptadecanoic acid, 2-butyltetradecanoic acid, isoarachic acid, 3-methylnonadecanoic acid, 2-ethyloctadecanoic acid, isohexacosanoic acid, 24-methylheptacosanoic acid, 2-ethyltetracosanoic acid, 2-butyldocosanoic acid, 2-hexylicosanoic acid, 2-octyloctadecanoic acid and 2-decylhexadecanoic acid. Those fatty acids can be used alone or in combination. Among those fatty acids, preferred are fatty acids having 8 to 18 carbon atoms, in particular, branched saturated fatty acids having 8 to 18 carbon atoms, such as isooctylic acid (preferably, 2-ethylhexanoic acid and 4,5-dimethylhexanoic acid), isononanoic acid (preferably, 2-ethylheptanoic acid and 3,5,5-trimethylhexanoic acid), isopalmitic acid, isotridecanoic acid, isostearic acid (preferably, methyl-branched isostearic acid, 2-heptylundecanoic acid and 2-isoheptylisoundecanoic acid), and the like.

With respect to the straight-chain fatty acids, there can be employed straight-chain fatty acids having 6 to 28 carbon atoms including straight-chain saturated fatty acids such as caproic acid, caprylic acid, octylic acid, nonylic acid, decanoic acid, dodecanoic acid, lauric acid, tridecanoic acid, myristic acid, palmitic acid, stearic acid, behenic acid and the like; and straight-chain unsaturated fatty acids such as caproleic acid, undecylenic acid, myristoleic acid, palmitoleic acid, oleic acid, elaidic acid, gondoic acid, erucic acid, brassidic acid and the like. Those fatty acids can be used alone or in combination.

The ester compound represented by formula (I) as the component (A) in the present invention includes one or more monoesters, diesters, triesters and tetraesters. The ester compound represented by formula (II) includes one or more monoesters and diesters. The ester compound represented by formula (I) and formula (II) means a mixture of two or more ester compounds separately selected from the ester compounds of formula (I) and the ester compounds of formula (II).

Further, with respect to the component (A) for use in the present invention, at least one of $R_1$ to $R_4$ in the formula (I) may preferably be hydrogen atom. Also, at least one of $R_5$ and $R_6$ in the formula (II) may preferably be hydrogen atom.

In the present invention, it is preferable that the ester compound includes diesters and triesters each of which has a basic skeleton represented by the above-mentioned formula (I) in an amount of 20 to 94 mass %, more preferably 40 to 80 mass % in total.

Preferably, the component (A) used in the present invention may be a mixture of reaction products of erythritol and/or erythritol condensate with isooctylic acid, represented by formula (I-1) and/or formula (II-1). In this case, it is preferable that the mixture contains the monoester, diester, triester and tetraester, each having a basic skeleton as represented by formula (I-1), in amounts of 0 to 10, 0 to 30, 18 to 70 and 6 to 75 mass %, respectively, more preferably, 0 to 3, 0 to 20, 13 to 70 and 8 to 60 mass %, respectively, and most preferably, 0 to 3, 3 to 20, 30 to 70 and 8 to 40, respectively. Also, it is preferable that the mixture contains the monoester and diester, each having a basic skeleton as represented by formula (II-1), in amounts of 0 to 10 and 0 to 50 mass % respectively, more preferably, 0 to 3 and 0 to 35 mass %, respectively, and most preferably, 0 to 3 and 5 to 35 mass %, respectively.

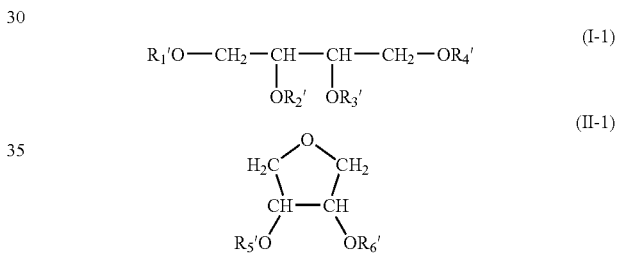

wherein $R_1'$ to $R_4'$ are each independently hydrogen atom or isooctylic acid residue and $R_5'$ and $R_6'$ are each independently hydrogen atom or isooctylic acid residue, provided that all of $R_1'$ to $R_4'$ do not represent hydrogen atom at the same time, and both of $R_5'$ and $R_6'$ do not represent hydrogen atom at the same time.

In the above formulas, the isooctylic acid residue includes —C(=O)—(CH$_2$CH$_3$)CH—(CH$_2$)$_3$—CH$_3$ [2-ethylhexanoic acid] and —C(=O)—(CH$_2$)$_2$—(CH$_3$)CH—(CH$_3$)CH—CH$_3$ [4,5-dimethylhexanoic acid].

The amount ratios of the monoester, diester, triester and tetraester previously specified in the case of the formula (I-1) apply to the case of formula (I); and the amount ratios of the monoester and diester previously specified in the case of the formula (II-1) apply to the case of formula (II).

The component (A) used in the present invention may particularly preferably be an ester compound(s) represented by formula (I) and/or formula (II) of erythritol and/or erythritol condensate with 2-ethylhexanoic acid.

The polycarboxylic acid used in the present invention to prepare the polycondensate as the component (A) in the present invention may preferably include dibasic carboxylic acids having 2 to 10 carbon atoms such as succinic acid, adipic acid, azelaic acid, sebacic acid and the like, and more preferably, dibasic saturated carboxylic acids having 4 to 10 carbon atoms. Those polycarboxylic acids can be used alone or in combination.

To prepare the polycondensate as the component (A) in the present invention, it is preferable to use as the raw material a mixture of a branched fatty acid (preferably, a branched saturated fatty acid) having 8 to 18 carbon atoms and a dibasic carboxylic acid having 2 to 10 carbon atoms (preferably, a dibasic carboxylic acid having 4 to 10 carbon atoms); and a mixture of a branched fatty acid (preferably, a branched saturated fatty acid) having 8 to 18 carbon atoms, a straight-chain fatty acid (a straight-chain saturated fatty acid) having 8 to 18 carbon atoms, and a dibasic carboxylic acid having 2 to 10 carbon atoms (preferably, a dibasic carboxylic acid having 4 to 10 carbon atoms). In this case, the branched fatty acid and the dibasic carboxylic acid may preferably be used with a molar ratio of branched fatty acid/dibasic carboxylic acid ranging from 70/30 to 95/5, and the branched fatty acid, the straight-chain fatty acid and the dibasic carboxylic acid may preferably be used with a molar ratio of (branched fatty acid and straight-chain fatty acid)/dibasic carboxylic acid ranging from 70/30 to 95/5.

The component (A) for use in the present invention preferably has a hydroxyl value "OHV" (hereinafter referred to as "OHV" simply) ranging from 10 to 150, more preferably 20 to 120, and most preferably 30 to 110. Particularly preferable among them is OHV ranging from 45 to 85. When the OHV is within the above-mentioned range, the compatibility with other oil components becomes better and the hydration tendency is improved to easily offer a moisturizing feel. The term OHV herein used is a value determined by the hydroxyl value measurement test method in accordance with the Japanese Standards of Quasi-drug Ingredients. Preferably, the component (A) for use in the present invention may assume a liquid state at room temperature, preferably having a viscosity at 25° C. of 30 to 30,000 mPa·s, more preferably 30 to 10,000 mPa·s, further more preferably 30 to 5,000 mPa·s, and most preferably 30 to 1,000 mPa·s. The viscosity is a value determined by the viscosity measurement test method 2 in accordance with the Japanese Standards of Quasi-drug Ingredients.

The component (A) for use in the present invention can be prepared, for example, by adding 1.5 to 3.5 equivalents of a fatty acid and/or polycarboxylic acid to one equivalent of erythritol, and carrying out a reaction of esterification and/or dehydration condensation at 180 to 240° C. in the absence or presence of a catalyst (e.g., tin chloride). After completion of the reaction, the catalyst is removed from the reaction mixture by adsorption treatment or the like, and low-molecular weight components including an unreacted raw material are eliminated by distillation or the like, thereby obtaining a final product.

Examples of silicone as the component (B) used in the present invention include silicone oils such as dimethylpolysiloxane, methylphenylpolysiloxane, octamethylcyclotetrasiloxane, decamethylcyclopentasiloxane, cross-linked polyether-modified silicone (such as (dimethicone/(PEG-10/15)) crosspolymer and (PEG-15/lauryl dimethicone) crosspolymer), alkyl-modified silicone, epoxy-modified silicone, and trimethylsiloxysilicate; amino-modified silicones such as aminopropylmethylsiloxane dimethylsiloxane copolymer, aminoethylaminopropylsiloxane dimethylsiloxane copolymer, and aminoethylaminopropylmethylsiloxane dimethylsiloxane copolymer; and silicone surfactants such as polyether-modified silicone (such as polyoxyethylene methylpolysiloxane copolymer, methylpolysiloxane cetylmethylpolysiloxane poly(oxyethylene oxypropylene) methylpolysiloxane copolymer). Preferred are dimethylpolysiloxane, methylphenylpolysiloxane, decamethylcyclopentasiloxane, amino-modified silicones, polyether-modified silicone, and cross-linked polyether-modified silicone. Meanwhile, PEG-3 dimethicone and PEG-10 dimethicone used in Examples are included in polyoxyethylene methylpolysiloxane copolymers. Among them, the component (B) may preferably be one or more members selected from the group consisting of dimethylpolysiloxane, methylphenylpolysiloxane, decamethylcyclopentasiloxane, and polyether-modified silicone.

The cosmetic preparation of the present invention comprises 20 mass % or more of an oil ingredient comprising the above components (A) and (B), and said oil ingredient comprising 50 mass % or more of the component (B).

Particularly, the cosmetic preparation may preferably comprise 25 mass % or more of an oil ingredient comprising the above components (A) and (B), and more preferably 30 mass % or more, e.g., 30 to 60 mass % thereof. In the present invention, it is preferable that the upper limit of an oil ingredient in the cosmetic preparation is 70 mass %, 60 mass % or 50 mass %.

Further, the content of the component (B) in the oil ingredient may preferably be 60 mass % or more, more preferably 75 mass % or more, and particularly preferably 80 mass % or 85 mass % or more. It is preferable that the upper limit of the component (B) in the oil ingredient is 95 mass %, 90 mass % or 80 mass %.

Meanwhile, the content of the component (A) in the oil ingredient may preferably be 5 mass % or more, 10 mass % or more, or 20 mass % or more. Among them, 5 to 40 mass % thereof is particularly preferable and 10 to 40 mass % thereof is more particularly preferable.

Though the oil ingredient in the cosmetic preparation of the present invention may preferably comprise the components (A) and (B), it is possible to contain a small amount of other oil ingredients such as hydrocarbons, ester oil agents, fatty acids, higher alcohols, fluorinated oil agents, lanolin derivatives and oil-soluble surfactants. The oil ingredient of the present invention means an oil component which is generally combined in a cosmetic preparation. Examples thereof include the component (A), the component (B), hydrocarbons, ester oil agents, fatty acids, higher alcohols, fluorinated oil agents, lanolin derivatives and oil-soluble surfactants.

The part other than the oil ingredient in the cosmetic preparation can be any one usually used in an intended cosmetic preparation, e.g., water and various solvents. The content of water in the cosmetic preparation may preferably be 30 to 70 mass %, and more preferably 30 to 60 mass %.

Accordingly, in addition to the above-mentioned components, various additional components can be incorporated into the formulation for the cosmetic preparation of the present invention if necessary so far as the effects of the present invention will not be damaged. For example, in order to fulfill the respective effects, it is possible to appropriately add a component usually combined in an intended cosmetic preparation, e.g., other oil ingredients such as hydrocarbons, esters, fatty acids, higher alcohols, fluorinated oil agents and lanolin derivatives (for instance, glyceryl tribehenate/isostearate/eicosandioate); water; various glycols such as propylene glycol, 1,3-butylene glycol, dipropylene glycol, hexylene glycol and polyethylene glycol; lower alcohols such as ethanol and butanol; powder materials such as titanium oxide; surfactants; UV light absorbers; moisturizing agents; water-base components such as those other than water, glycols and lower alcohols; inorganic salts such as sodium chloride; organic salts; film-forming agents; anti-browning agents; antioxidants; anti-foamers; beauty ingredients; preservatives such as methylparaben; various plant extracts; and perfumes.

Particularly, the present invention has the advantage that it is excellent in an affinity for a water-base component such as water, ethanol, 1,3-butylene glycol and glycerin each of which is contained in the cosmetic preparation.

Examples of an intended cosmetic preparation in the present invention include makeup cosmetic preparations such as foundations, water-in-oil emulsified liquid foundations and mascara; skin-care cosmetic preparations such as emulsions and creams; sunscreen agents; two-layer separative makeup removers; and two-layer separative hair dressings. Particularly, the cosmetic preparation of the present invention can preferably be used in water-in-oil cosmetic preparations such as water-in-oil creams and water-in-oil sunscreen creams; two-layer separative makeup removers (also referred to as multiple phase separative cleansing agents or two-layer separative cleansing agents); or two-layer separative hair dressings.

More specifically, in the intended cosmetic preparation of the present invention, and particularly in the case of a water-in-oil cosmetic preparation, it is preferable to use a silicone surfactant as the component (B). In this case, though a surfactant other than a silicone surfactant can also be combined, it is preferable not to combine a surfactant other than a silicone surfactant. When using a silicone surfactant, 0.5 to 7 mass % thereof may preferably be comprised in the cosmetic preparation, and 1 to 5 mass % thereof may more preferably be comprised therein.

In the case of preparing a two-layer separative makeup remover or a two-layer separative hair dressing, it is possible to prepare a two-layer separative makeup remover or a two-layer separative hair dressing each of which comprises the above components (A) and (B) in an arbitrarily-selected ratio. In such a case, even if silicone is combined therein in high concentrations, it is possible to sustain the emulsified state of the oil ingredient of the present invention in use without a surfactant. Thus, it is preferable to prepare them without using either a silicone surfactant or a surfactant other than a silicone surfactant.

In the case of preparing a two-layer separative makeup remover, the above various preferable conditions can be applied, and said remover may preferably comprises 20 to 60 mass % of an oil ingredient comprising the components (A) and (B), and 30 to 80 mass % in total of a water-soluble solvent and water (more preferably 50 mass % or more thereof). It is possible to use a water-soluble solvent such as various glycols, e.g., propylene glycol, 1,3-butylene glycol, dipropylene glycol, hexylene glycol and polyethylene glycol; and alkyl ethers or alkyl esters thereof, e.g., those disclosed in JP 10-101529 A, JP 2002-114636 A, JP 2003-192535 A, and the like.

In the case of preparing a two-layer separative hair dressing, the above various preferable conditions can be applied, and said hair dressing may preferably comprises 20 to 60 mass % of an oil ingredient comprising the components (A) and (B), and 30 to 80 mass % in total of a water-soluble solvent and water (more preferably 50 mass % or more thereof). Further, in order to smooth and supple hair, it is possible to add a cationic polymer to a water phase. The cationic polymer used in the present invention can be any one usually used in a cosmetic preparation. Examples thereof include cationized cellulose derivatives, cationic starch, cationized guar gum derivatives, cationized fenugreek gum derivatives, cationized tara gum derivatives, cationized locust bean gum derivatives, homopolymers of diallyl quaternary ammonium salts, diallyl quaternary ammonium salt/acrylamide copolymers, quaternized polyvinyl pyrrolidone derivatives, polyglycol-polyamine condensates, vinylimidazolium trichloride/vinylpyrrolidone copolymer, hydroxyethylcellulose/dimethyl diallyl ammonium chloride copolymer, vinylpyrrolidone/quaternized dimethylaminoethyl methacrylate copolymers, polyvinylpyrrolidone/alkyl aminoacrylate copolymers, polyvinylpyrrolidone/alkyl aminoacrylate/vinylcaprolactam copolymers, vinylpyrrolidone/methacrylamidopropylchlorotrimethyl ammonium copolymer, alkylacrylamide/acrylate/alkylaminoalkylacrylamide/polyethylene glycol methacrylate copolymers, adipic acid/dimethylaminohydroxypropylethylenetriamine copolymer, N,N-dimethylaminoethyl methacrylate-vinylpyrrolidone copolymer diethyl sulfate salt, and methyl-vinylimidazolium chloride/vinylpyrrolidone copolymers. Preferred are cationized cellulose derivatives, cationized guar gum derivatives, N,N-dimethylaminoethyl methacrylate-vinylpyrrolidone copolymer diethyl sulfate salt, and methyl-vinylimidazolium chloride/vinylpyrrolidone copolymers. The two-layer separative hair dressing of the present invention may preferably comprise 0.1 to 5 mass % of a cationic polymer.

The present invention will now be explained in detail by referring to the following examples, which are not intended to be limiting of the present invention.

EXAMPLES

Preparation of Erythritol Fatty Acid Ester

Preparation Example 1

Preparation of Ester Compound of Erythritol and 2-ethylhexanoic acid

A four-necked flask (300 mL) equipped with a stirrer, a thermometer, a nitrogen gas inlet, and a reflux condenser was charged with 178 g (1.24 mol) of 2-ethylhexanoic acid (octylic acid made by Kyowa Hakko Kogyo Co., Ltd.) and 72 g (0.59 mol) of erythritol (erythritol made by Nikken Chemicals Co., Ltd.). Xylene was added as a solvent for reflux in an amount of 5 mass % of the total mass of the charged materials. The mixture was allowed to react at 180 to 240° C. for 20 hours with stirring. After completion of the reaction, xylene serving as the solvent for reflux was distilled away under reduced pressure, the decolorization treatment was carried out using activated clay and deodorization and distillation were performed by the conventional methods, so that 142 g of a desired ester compound of erythritol and 2-ethylhexanoic acid of Preparation Example 1 was obtained.

The contents of monoester, diester, triester and tetraester having the basic skeleton of formula (I), and the contents of monoester and diester having the basic skeleton of formula (II) were found to be the following.

Monoester having the basic skeleton of formula (I): 0 mass %

Diester having the basic skeleton of formula (I): 7.7 mass %

Triester having the basic skeleton of formula (I): 41.5 mass %

Tetraester having the basic skeleton of formula (I): 20.4 mass %

Monoester having the basic skeleton of formula (II): 0 mass %

Diester having the basic skeleton of formula (II): 28.9 mass %

Further, this ester compound had a hydroxyl value of 63, and a viscosity at 25° C. of 72 mPa·s which was measured by Brookfield viscometer.

Referential Example 1

Evaluation of Compatibility with Silicone 10 g of the ester compound of Preparation Example 1 and each 10 g of various silicones in Table 1 (the ester compound of Preparation Example 1: each various silicones=1:1 by mass ratio) were mixed and stirred, and then left to stand at room temperature for 24 hours. Then, the compatibility of the ester compound of Preparation Example 1 with silicone was evaluated by visually confirming the state of the sample. The evaluation was conducted in accordance with the following standards. Besides, compatibilities of diisostearyl malate (trade name: Cosmol 222 made by Nisshin OilliO Group, Ltd.) and diglyceryl triisostearate (trade name: Cosmol 43V made by Nisshin OilliO Group, Ltd.) with silicone were also evaluated by the same method as above, each of which is an oil agent excellent in pigmentary dispersibility and widely used in a cosmetic preparation. The results are shown in Table 1.

Evaluation Standards of Compatibility with Silicone
○: completely dissolved
Δ: uniformly clouding
x: completely separated

TABLE 1

Evaluation results of compatibility with silicone

|  | Ester compound of Preparation Example 1 | Diisostearyl malate | Diglyceryl triisostearate |
|---|---|---|---|
| Decamethylcyclopentasiloxane *1 | 1:1 | ○ | ○ | ○ |
| Dimethyl polysiloxane *2 | 1:1 | ○ | ○ | X |
| PEG-3 dimethicone *3 | 1:1 | ○ | ○ | X |
| PEG-10 dimethicone *4 | 1:1 | ○ | Δ | X |
| Methylpolysiloxane cetylmethylpolysiloxane poly(oxyethylene oxypropylene) methylpolysiloxane copolymer *5 | 1:1 | ○ | ○ | ○ |
| (Dimethicone/(PEG-10/15)) crosspolymer *6 | 1:1 | ○ | Δ | Δ |
| (PEG-15/lauryl dimethicone) crosspolymer *7 | 1:1 | ○ | Δ | X |

*1 SH245 made by Dow Corning Toray
*2 KF-96A-10cs made by Shin-Etsu Chemical Co., Ltd.
*3 KF-6015 made by Shin-Etsu Chemical Co., Ltd.
*4 KF-6017 made by Shin-Etsu Chemical Co., Ltd.
*5 ABIL EM90 made by Evonik Goldschmidt GmbH
*6 KSG-210 made by Shin-Etsu Chemical Co., Ltd.
*7 KSG-310 made by Shin-Etsu Chemical Co., Ltd.

As clarified from Table 1, the ester compound of Preparation Example 1 had a high compatibility with silicone.

Diisostearyl malate had a relatively-high compatibility with silicone. On the other hand, diglyceryl triisostearate had a low compatibility with silicone.

Example 1

Water-in-Oil Cream

Components 1 to 6 in Table 2 were sufficiently stirred at 70° C. and prepared as an oil phase. Components 7 to 10 heated to 70° C. were gradually added thereto and emulsified using a homo mixer (trade name: Desktop quick homo mixer LR-1 made by Mizuho Industrial Co., Ltd.). Then, the reaction mixture was cooled down to prepare a water-in-oil cream.

The water-in-oil cream was evaluated in accordance with the following method and standards.

10 subjects used the water-in-oil cream and evaluated it on a 3-point scale (good: 2, okay: 1, bad: 0) about each items of the spreading and non-greasy states thereof. These points were defined as a sensory evaluation. Further, a total of the sensory evaluations of each subjects was defined as a comprehensive evaluation. The comprehensive evaluation was evaluated in accordance with the following standards.

Evaluation Standards of a Comprehensive Evaluation
○: a total point is 15 or more
Δ: a total point is 10 or more and less than 15
x: a total point is less than 10

TABLE 2

Combination (mass %) of water-in-oil cream and evaluation results

|  |  |  | Example 1 | Comparative Example 1 |
|---|---|---|---|---|
| (A) | 1 | Ester compound of Preparation Example 1 | 7 | — |
| (B) | 2 | Decamethylcyclopentasiloxane *1 | 15 | 15 |
|  | 3 | Dimethyl polysiloxane *2 | 3 | 3 |
|  | 4 | Methylpolysiloxane cetylmethylpolysiloxane poly(oxyethylene oxypropylene) methylpolysiloxane copolymer *3 | — | 3 |
|  | 5 | PEG-10 dimethicone *4 | 3 | — |
|  | 6 | Diisostearyl malate *5 | — | 7 |
|  | 7 | 1,3-Butylene glycol | 5 | 5 |
|  | 8 | Sodium chloride | 1 | 1 |
|  | 9 | Methylparaben | 0.1 | 0.1 |
|  | 10 | Purified water | 65.9 | 65.9 |

TABLE 2-continued

Combination (mass %) of water-in-oil cream and evaluation results

|  |  | Example 1 | Comparative Example 1 |
|---|---|---|---|
|  | Total | 100 | 100 |
| Eval. Results | Spreading state | ○ | Δ |
|  | Non-greasy state | ○ | Δ |

*1 SH245 made by Dow Corning Toray
*2 KF-96A-10cs made by Shin-Etsu Chemical Co., Ltd.
*3 ABIL EM90 made by Evonik Goldschmidt GmbH
*4 KF-6017 made by Shin-Etsu Chemical Co., Ltd.
*5 COSMOL 222 made by Nisshin OilliO Group, Ltd.

As clarified from Table 2, the water-in-oil cream of Example 1 in which the ester compound of Preparation Example 1 was combined had a good feeling (spreading and non-greasy states) in use.

On the other hand, the water-in-oil cream of Comparative Example 1 in which diisostearyl malate having a relatively-high compatibility with silicone was combined was inferior in a feeling (spreading and non-greasy states) in use to the water-in-oil cream of Example 1.

Example 2

Water-in-Oil Sunscreen Cream

Components 1 to 4 in Table 3 were sufficiently stirred at 70° C. and components 5 to 7 were added thereto to prepare an oil phase. Then, components 8 to 11 heated to 70° C. were gradually added thereto and emulsified using a homo mixer. Then, the reaction mixture was cooled down to prepare a water-in-oil sunscreen cream.

The water-in-oil sunscreen cream was evaluated in accordance with the following method and standards.
(Evaluation of the Touch)

10 subjects used the water-in-oil sunscreen cream and evaluated it on a 3-point scale (good: 2, okay: 1, bad: 0) about the touch of the cream. These points were defined as a sensory evaluation. Further, a total of the sensory evaluations of each subjects was defined as a comprehensive evaluation. The comprehensive evaluation was evaluated in accordance with the following standards.
Evaluation Standards of a Comprehensive Evaluation of the Touch
○: a total point is 15 or more
Δ: a total point is 10 or more and less than 15
×: a total point is less than 10

TABLE 3

Combination (mass %) of water-in-oil sunscreen cream and evaluation results

|  |  |  | Example 2 | Comparative Example 2 |
|---|---|---|---|---|
| (A) | 1 | Ester compound of Preparation Example 1 | 4.5 | — |
| (B) | 2 | Decamethylcyclopentasiloxane *1 | 13.5 | 13.5 |
|  | 3 | Dimethyl polysiloxane *2 | 9 | 9 |
|  | 4 | PEG-10 dimethicone *3 | 3 | 3 |
|  | 5 | Titanium oxide *4 | 10 | 10 |
|  | 6 | Glyceryl tribehenate/ isostearate/eicosandioate *5 | 3 | 3 |
|  | 7 | Diisostearyl malate *6 | — | 4.5 |
|  | 8 | 1,3-Butylene glycol | 5 | 5 |
|  | 9 | Sodium chloride | 1 | 1 |

TABLE 3-continued

Combination (mass %) of water-in-oil sunscreen cream and evaluation results

|  |  | Example 2 | Comparative Example 2 |
|---|---|---|---|
|  | 10 Methylparaben | 0.1 | 0.1 |
|  | 11 Purified water | 50.9 | 50.9 |
|  | Total | 100 | 100 |
|  | Touch | ○ | Δ |

*1 SH245 made by Dow Corning Toray
*2 KF-96A-10cs made by Shin-Etsu Chemical Co., Ltd.
*3 KF-6017 made by Shin-Etsu Chemical Co., Ltd.
*4 MT-500B made by Teika Co., Ltd.
*5 NOMCORT SG made by Nisshin OilliO Group, Ltd.
*6 COSMOL 222 made by Nisshin OilliO Group, Ltd.

As clarified from Table 3, the water-in-oil sunscreen cream of Example 2 in which the ester compound of Preparation Example 1 was combined had a good feeling (touch) in use.

On the other hand, the water-in-oil sunscreen cream of Comparative Example 2 in which diisostearyl malate having a relatively-high compatibility with silicone was combined was inferior in a feeling (touch) in use to the water-in-oil sunscreen cream of Example 2.

Example 3

Two-Layer Separative Makeup Remover

Components 5 to 8 which were previously dissolved by heating at 70° C. were added to components 1 to 4 in Table 4 to prepare a two-layer separative makeup remover.

The obtained two-layer separative makeup remover was evaluated in accordance with the following method and standards.
(Evaluation of Emulsified State Retention Time)

In order to evaluate the retention time of the emulsified state of the two-layer separative makeup remover, the two-layer separative makeup remover was strongly shaken in a glass container 30 times to be uniformly mixed. Then, it was left to stand at room temperature, and the retention time of the emulsified state thereof was measured. The retention time of the emulsified state thereof was evaluated in accordance with the following standards, and ○ was accepted.

A two-layer separative makeup remover is used by lightly shaking it and temporarily emulsifying the oil phase and the water phase thereof. When the time for returning to a former two-layer separative state is too fast, it is inconvenient for use. Therefore, the longer the retention time of the emulsified state of the two-layer separative makeup remover becomes, the more convenient it is for use.
Evaluation Standards of the Emulsified State Retention Time
○: retention time is 3 minutes or more
Δ: retention time is 1 minute or more and less than 3 minutes
×: retention time is less than 1 minute
(Evaluation of Feeling after Washing)

10 subjects used the two-layer separative makeup remover and evaluated it on a 3-point scale (good: 2, okay: 1, bad: 0) about the feeling after flushing the remover with water. These points were defined as a sensory evaluation. Further, a total of the sensory evaluations of each subjects was defined as a comprehensive evaluation. The comprehensive evaluation was evaluated in accordance with the following standards.
Evaluation Standards of a Comprehensive Evaluation of Feeling after Washing
○: a total point is 15 or more Δ: a total point is 10 or more and less than 15
x: a total point is less than 10

TABLE 4

Combination (mass %) of two-layer separative makeup remover and evaluation results

|     |   |                              | Present invention | | | Comparative Example | |
|-----|---|------------------------------|------|------|------|------|------|
|     |   |                              | 1    | 2    | 3    | 3    | 4    |
| (A) | 1 | Ester compound of Preparation Example 1 | 5 | 15 | 15 | — | — |
| (B) | 2 | Decamethylcyclopentasiloxane *1 | 35 | 25 | — | 40 | 25 |
|     | 3 | Dimethyl polysiloxane *2     | —    | —    | 25   | —    | —    |
|     | 4 | Diisostearyl malate *3       | —    | —    | —    | —    | 15   |
|     | 5 | 1,3-Butylene glycol          | 20   | 20   | 20   | 20   | 20   |
|     | 6 | Sodium chloride              | 1    | 1    | 1    | 1    | 1    |
|     | 7 | Purified water               | 38.9 | 38.9 | 38.9 | 38.9 | 38.9 |
|     | 8 | Methylparaben                | 0.1  | 0.1  | 0.1  | 0.1  | 0.1  |
| Total |  |                             | 100  | 100  | 100  | 100  | 100  |
| Eval. Results | | Emulsified state retention time | ○ | ○ | ○ | X | ○ |
|     |   | Feeling after washing        | ○    | ○    | ○    | Δ    | X    |

*1 SH245 made by Dow Corning Toray
*2 KF-96A-10cs made by Shin-Etsu Chemical Co., Ltd.
*3 COSMOL 222 made by Nisshin OilliO Group, Ltd.

As clarified from Table 4, the two-layer separative makeup remover of each of the present inventions 1 to 3 in which the ester compound of Preparation Example 1 was combined had a good retention time of the emulsified state thereof and a good feeling (feeling after washing) in use.

On the other hand, the separative makeup remover of Comparative Example 3 in which no oil agent was combined was inferior in the retention time of the emulsified state and a feeling (feeling after washing) in use to the separative makeup removers of the present inventions 1 to 3. Further, the two-layer separative makeup remover of Comparative Example 4 in which diisostearyl malate having a relatively-high compatibility with silicone was combined had a good retention time of the emulsified state thereof, but it was inferior in a feeling (feeling after washing) in use to the separative makeup removers of the present inventions 1 to 3.

Example 4

Two-Layer Separative Hair Dressing

Components 6 to 11 which were previously dissolved by heating at 70° C. were added to components 1 to 5 in Table 5 to prepare a two-layer separative hair dressing.

The obtained two-layer separative hair dressing was evaluated in accordance with the following method and standards.
(Evaluation of Emulsified State Retention Time)

In order to evaluate the retention time of the emulsified state of the two-layer separative hair dressing, the two-layer separative hair dressing was strongly shaken in a glass container 30 times to be uniformly mixed. Then, it was left to stand at room temperature, and the retention time of the emulsified state thereof was measured. The retention time of the emulsified state thereof was evaluated in accordance with the following standards, and ○ was accepted.

A two-layer separative hair dressing is used by lightly shaking it and temporarily emulsifying the oil phase and the water phase thereof. When the time for returning to a former two-layer separative state is too fast, it is inconvenient for use. Therefore, the longer the retention time of the emulsified state of the two-layer separative hair dressing becomes, the more convenient it is for use.
Evaluation Standards of the Emulsified State Retention Time
○: retention time is 3 minutes or more
Δ: retention time is 1 minute or more and less than 3 minutes
x: retention time is less than 1 minute
(Evaluation of Non-Greasy and Moisturizing States of Hair)

A human hair wig was treated with marketed normal-type shampoo and rinse and dried. Next, 5 g of each sample of present inventions 4 to 7 was applied to the human hair wig and dried. Then, non-greasy and moisturizing states of the wig were evaluated on a 3-point scale (good: 2, okay: 1, bad: 0). These points were defined as a sensory evaluation. Further, a total of the evaluation results of each raters was defined as a comprehensive evaluation. The comprehensive evaluation was evaluated in accordance with the following standards.
○: a total point is 15 or more
Δ: a total point is 10 or more and less than 15
x: a total point is less than 10

TABLE 5

Combination (mass %) of two-layer separative hair dressing and evaluation results

|     |   |                              | Present invention | | | | Comparative Example | |
|-----|---|------------------------------|----|----|----|----|----|----|
|     |   |                              | 4  | 5  | 6  | 7  | 5  | 6  |
| (A) | 1 | Ester compound of Preparation Example 1 | 10 | 10 | 10 | 10 | — | — |
| (B) | 2 | Decamethylcyclopentasiloxane *1 | 28 | 28 | 28 | 28 | 38 | 28 |
|     | 3 | Dimethyl polysiloxane *2     | 2  | —  | —  | 2  | 2  | 2  |
|     | 4 | Dimethyl polysiloxane *3     | —  | 2  | —  | —  | —  | —  |
|     | 5 | Dimethyl polysiloxane *4     | —  | —  | 2  | —  | —  | —  |
|     | 6 | Diisostearyl malate *5       | —  | —  | —  | —  | —  | 10 |
|     | 7 | N,N-dimethylaminoethyl methacrylate-vinylpyrrolidone copolymer diethyl sulfate salt (20% aqueous solution) *6 | 3 | 3 | 3 | — | 3 | 3 |
|     | 8 | Hydroxyethylcellulose hydroxypropyl | — | — | — | 3 | — | — |

TABLE 5-continued

Combination (mass %) of two-layer separative hair dressing and evaluation results

| | | Present invention | | | | Comparative Example | |
|---|---|---|---|---|---|---|---|
| | | 4 | 5 | 6 | 7 | 5 | 6 |
| | trimethylammonium chloride ether *7 | | | | | | |
| 9 | 1,3-Butylene glycol | 20 | 20 | 20 | 20 | 20 | 20 |
| 10 | Sodium chloride | 1 | 1 | 1 | 1 | 1 | 1 |
| 11 | Purified water | 35.9 | 35.9 | 35.9 | 35.9 | 35.9 | 35.9 |
| 12 | Methylparaben | 0.1 | 0.1 | 0.1 | 0.1 | 0.1 | 0.1 |
| Total | | 100 | 100 | 100 | 100 | 100 | 100 |
| Eval. Results | Emulsified state retention time | ○ | ○ | ○ | ○ | X | ○ |
| | Non-greasy state | ○ | ○ | ○ | ○ | ○ | X |
| | Moisturizing state | ○ | ○ | ○ | ○ | Δ | ○ |

*1 SH245 made by Dow Corning Toray
*2 KF-96A-10cs made by Shin-Etsu Chemical Co., Ltd.
*3 KF-96H-30,000cs made by Shin-Etsu Chemical Co., Ltd.
*4 KF-96H-500,000cs made by Shin-Etsu Chemical Co., Ltd.
*5 COSMOL 222 made by Nisshin OilliO Group, Ltd.
*6 GAFQUAT 755N made by ISP Japan Ltd.
*7 POIZ C-60H made by Kao Corporation As clarified from Table 5, the two-layer separative hair dressing of each of the present inventions 4 to 7 in which the ester compound of Preparation Example 1 was combined had a good retention time of the emulsified state thereof and a good non-greasy and moisturizing states of hair.

On the other hand, the two-layer separative hair dressing of Comparative Example 5 in which no oil agent was combined was inferior in the retention time of the emulsified state and the moisturizing state of hair to the two-layer separative hair dressings of the present inventions 4 to 7. Further, the two-layer separative hair dressing of Comparative Example 6 in which diisostearyl malate having a relatively-high compatibility with silicone was combined had a good retention time of the emulsified state thereof and a good moisturizing state of hair, but it was inferior in the non-greasy state of hair to the two-layer separative hair dressings of the present inventions 4 to 7.

What is claimed is:

1. A cosmetic preparation which comprises an oil ingredient comprising the following components (A) and (B), said oil ingredient comprising 50 mass % or more of the component (B):

(A): one or more members selected from the group consisting of i.) an ester compound(s) represented by the following formula (I) and/or formula (II) which are reaction products of erythritol and/or erythritol condensate with a fatty acid(s); ii.) polycondensates of erythritol and/or erythritol condensate, the above-mentioned ester compound(s) and a polycarboxylic acid(s); iii.) polycondensates of a fatty acid(s) with a polycondensate(s) of erythritol and/or erythritol condensate with a polycarboxylic acid(s); and iv.) polycondensates of erythritol and/or erythritol condensate, a fatty acid(s) and a polycarboxylic acid(s),

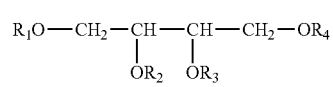

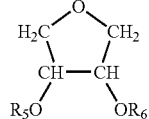

wherein $R_1$ to $R_4$ are each independently a hydrogen atom or a fatty acid residue, and $R_5$ and $R_6$ are each independently a hydrogen atom or a fatty acid residue, provided that all of $R_1$ to $R_4$ do not represent hydrogen atom at the same time, and both of $R_5$ and $R_6$ do not represent hydrogen atom at the same time; and (B): silicone oil;

wherein the cosmetic preparation does not comprise a surfactant and is a two-layer separative makeup remover or a two-layer separative hair dressing that is shaken before use and wherein one layer of the separative makeup remover or separative hair dressing comprises the oil ingredient and the other layer comprises an aqueous phase.

2. The cosmetic preparation according to claim 1, wherein the content of the oil ingredient is 30 mass % or more of the cosmetic preparation.

3. The cosmetic preparation according to claim 1, wherein the content of the component (B) in the oil ingredient is 75 mass % or more.

4. The cosmetic preparation according to claim 1, wherein the content of the component (A) in the oil ingredient is 5 mass % or more.

5. The cosmetic preparation according to claim 1, wherein the component (A) is an ester compound(s) represented by formula (I) and/or formula (II) of erythritol and/or erythritol condensate with 2-ethylhexanoic acid.

6. The cosmetic preparation according to claim 1, wherein the component (B) is one or more members selected from the group consisting of dimethylpolysiloxane, methylphenylpolysiloxane, and decamethylcyclopentasiloxane.

7. The cosmetic preparation according to claim 1, wherein the content of the oil ingredient is 20 mass % or more of the cosmetic preparation.

* * * * *